United States Patent
Chaney et al.

(10) Patent No.: US 9,730,706 B2
(45) Date of Patent: Aug. 15, 2017

(54) METHOD OF USING A FEMORAL SURGICAL INSTRUMENT

(71) Applicant: DEPUY IRELAND UNLIMITED COMPANY, CO Cork (IE)

(72) Inventors: Rebecca L. Chaney, Warsaw, IN (US); Craig S. Tsukayama, Fort Wayne, IN (US); Janelle M. Lubensky, Winona Lake, IN (US); Duncan G. Young, Yorkshire (GB); Jonathan C. Lee, Mishawaka, IN (US); Jeffrey M. Walcutt, Fort Wayne, IN (US); Francisco A. Amaral, Acushnet, MA (US); Carl F. Livorsi, Lakeville, MA (US); Peter J. James, Nottingham (GB)

(73) Assignee: DEPUY IRELAND UNLIMITED COMPANY, Co Cork (IE)

( * ) Notice: Subject to any disclaimer, the term of this patent is extended or adjusted under 35 U.S.C. 154(b) by 0 days.

(21) Appl. No.: 14/835,523

(22) Filed: Aug. 25, 2015

(65) Prior Publication Data
US 2016/0015399 A1    Jan. 21, 2016

Related U.S. Application Data

(62) Division of application No. 13/834,374, filed on Mar. 15, 2013, now Pat. No. 9,113,918.

(51) Int. Cl.
*A61B 17/16* (2006.01)
*A61B 17/15* (2006.01)
(Continued)

(52) U.S. Cl.
CPC .......... *A61B 17/155* (2013.01); *A61B 17/164* (2013.01); *A61B 17/1659* (2013.01);
(Continued)

(58) Field of Classification Search
CPC .............. A61B 17/164; A61B 17/1659; A61B 17/1675; A61B 17/155; A61B 17/1717;
(Continued)

(56) References Cited

U.S. PATENT DOCUMENTS 5,674,223 A * 10/1997 Cipolletti ............. A61B 17/155
606/85
5,792,143 A * 8/1998 Samuelson ........... A61F 2/4607
606/102
(Continued)

FOREIGN PATENT DOCUMENTS

EP    2338422 A1    6/2011
FR    2917282 A1    12/2008
(Continued)

OTHER PUBLICATIONS

Extended European Search Report, European Application No. 14159568.6-1654/2786715, dated Dec. 10, 2014, 12 pages.
(Continued)

*Primary Examiner* — David Bates
*Assistant Examiner* — Olivia C Chang
(74) *Attorney, Agent, or Firm* — Barnes & Thornburg LLP

(57) ABSTRACT

A method of using an orthopedic surgical instrument assembly that includes an instrument handle configured to clamp a broach and femoral stem trial assembly. A depth stop is configured to removably couple to the instrument handle. When the broach and femoral stem trial are advanced into a medullary canal of a patient's femur, a substantially planar proximal surface of the depth stop is configured to engage the distal surface of the femur, determining the depth of the broach in the medullary canal. The proximal surface of the depth stop is parallel to the joint line, defining an oblique angle to the anatomical axis of the femur. The depth stop
(Continued)

may be attached to the instrument handle at a number of positions to control the depth of the broach. The assembly may include a spacer plate removably coupled to the depth stop that distalizes the broach in the medullary canal.

6 Claims, 15 Drawing Sheets

(51) Int. Cl.
  *A61B 17/17* (2006.01)
  *A61F 2/46* (2006.01)
  *A61B 17/92* (2006.01)
  *A61B 17/00* (2006.01)
  *A61B 90/00* (2016.01)

(52) U.S. Cl.
  CPC ...... *A61B 17/1675* (2013.01); *A61B 17/1717* (2013.01); *A61B 17/1735* (2013.01); *A61B 17/1764* (2013.01); *A61B 17/921* (2013.01); *A61F 2/461* (2013.01); *A61B 2017/0046* (2013.01); *A61B 2090/034* (2016.02); *A61B 2090/062* (2016.02); *A61B 2090/0811* (2016.02); *A61F 2/4657* (2013.01); *A61F 2/4684* (2013.01); *A61F 2002/4623* (2013.01); *A61F 2002/4624* (2013.01); *A61F 2002/4681* (2013.01)

(58) Field of Classification Search
  CPC .... A61B 17/1764; A61F 2/4683; A61F 2/461; A61F 2002/4624; A61F 2002/4662
  See application file for complete search history.

(56) References Cited

U.S. PATENT DOCUMENTS

| | | | |
|---|---|---|---|
| 5,931,841 A * | 8/1999 | Ralph | A61B 17/1659 407/18 |
| 6,663,636 B1 | 12/2003 | Lin | |
| 7,998,215 B2 | 8/2011 | Frey et al. | |
| 2008/0033444 A1 | 2/2008 | Bastian et al. | |
| 2008/0077241 A1 | 3/2008 | Nguyen | |
| 2010/0121331 A1 | 5/2010 | Sharp et al. | |
| 2011/0160733 A1 | 6/2011 | Wallstein | |
| 2012/0191205 A1 | 7/2012 | Bojarski et al. | |
| 2012/0259338 A1 | 10/2012 | Carr et al. | |

FOREIGN PATENT DOCUMENTS

| | | |
|---|---|---|
| FR | 2926208 A1 | 7/2009 |
| WO | 2012001385 | 2/2012 |

OTHER PUBLICATIONS

Extended European Search Report, European Application No. 14158783.2-1654, dated Jul. 18, 2014, 7 pages.
Zimmer NexGen LCCK, Surgical Technique for use with LCCK 4-in-1 Instrument, 2009, 52 pages.
DePuy Orthopaedics, Inc., Sigma Revision and M.B.T. Revision Tray, Surgical Technique, 2008, 82 pages.
Smith & Nephew, Legion, Revision Knee System, Surgical Technique, 2005, 40 pages.
Biomet, Vanguard SSK, Revision System, Surgical Technique, Feb. 2008, 64 pages.
GMK Revision, Surgical Technique, Ref. 99.27.12US rev. 1, 1999, 74 pages.
PFC Sigma RP-F, Specialist 2 Instruments, Surgical Technique, Performance in Flexion, 2007, 32 pages.
P.F.C. Sigma Rotating Platform Knee System with M.B.T. Tray, Primary Procedure with a Curved or Posterior Stablised Implant, 2003, 43 pages.
LCS High Performance Instruments, Surgical Technique, 2008, 44 pages.
Sigma High Performance Instruments, Design Rationale, 2007, 12 pages.
Sigma High Performance Instruments, Classic Surgical Technique, 2010, 52 pages.
Attune Knee System Surgical Technique, 2013, 73 pages.

* cited by examiner

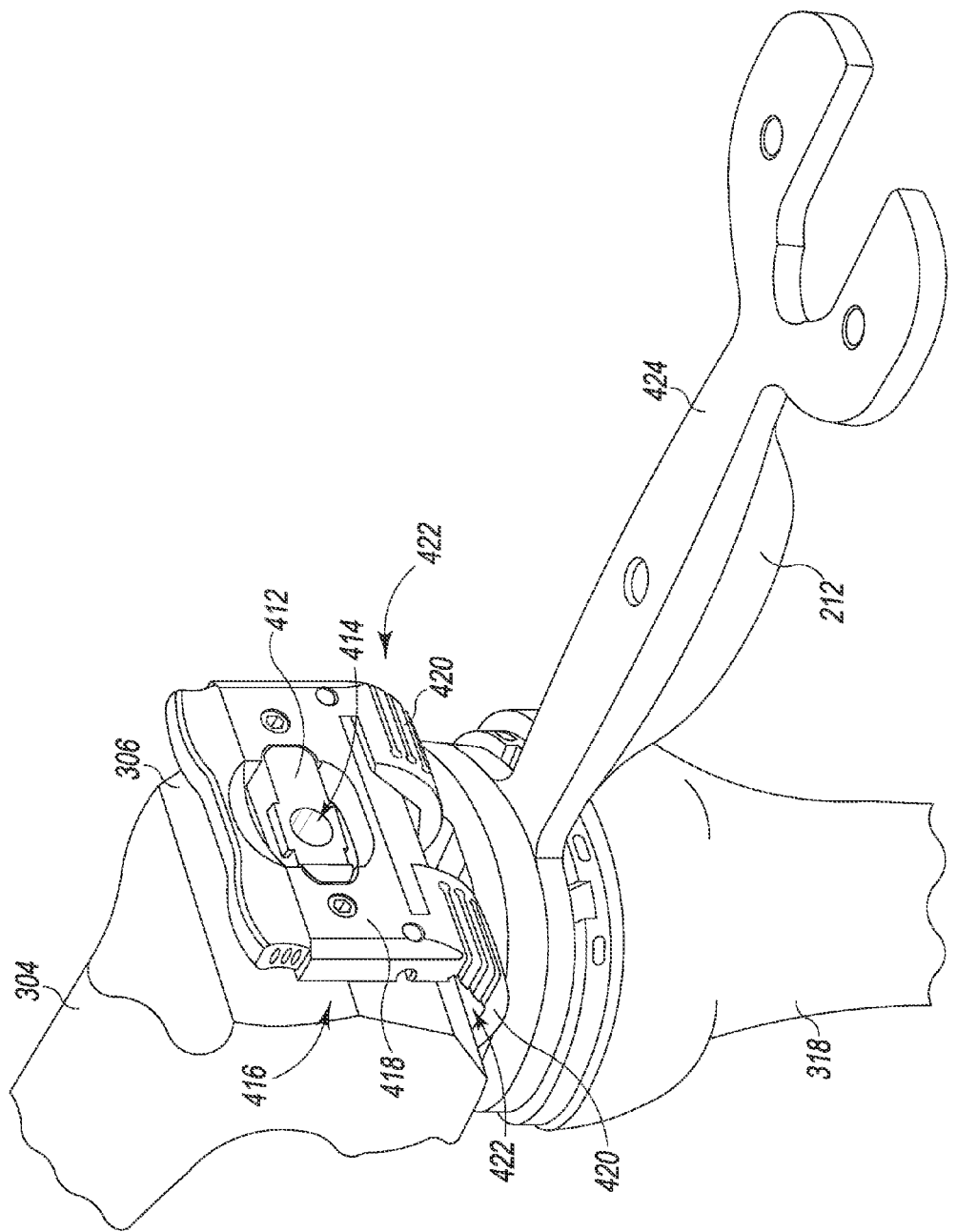

METHOD OF USING A FEMORAL SURGICAL INSTRUMENT

This application is a divisional of U.S. patent application Ser. No. 13/834,374, filed Mar. 15, 2013, which is hereby incorporated by reference.

CROSS-REFERENCE

Cross reference is made to copending U.S. patent application Ser. No. 13/834,862 entitled "FEMORAL SYSTEM HANDLE SURGICAL INSTRUMENT AND METHOD OF ASSEMBLING SAME," which is assigned to the same assignee as the present application, filed concurrently herewith, and hereby incorporated by reference.

TECHNICAL FIELD

The present disclosure relates generally to orthopedic instruments for use in the performance of an orthopedic joint replacement procedure, and more particularly to orthopedic surgical instruments for use in the performance of a knee replacement procedure.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. The tibial tray generally includes a plate having a stem extending distally therefrom, and the femoral component generally includes a pair of spaced apart condylar elements, which include surfaces that articulate with corresponding surfaces of the polymer bearing. The stem of the tibial tray is configured to be implanted in a surgically-prepared medullary canal of the patient's tibia, and the femoral component is configured to be coupled to a surgically-prepared distal end of a patient's femur.

From time-to-time, a revision knee surgery may need to be performed on a patient. In such a revision knee surgery, the previously-implanted knee prosthesis is surgically removed and a replacement knee prosthesis is implanted. In some revision knee surgeries, all of the components of the previously-implanted knee prosthesis, including, for example, the tibial tray, the femoral component, and the polymer bearing, may be surgically removed. In other revision knee surgeries, only part of the previously-implanted knee prosthesis may be removed and replaced.

During a revision knee surgery, the orthopedic surgeon typically uses a variety of different orthopedic surgical instruments such as, for example, cutting blocks, surgical reamers, drill guides, prosthetic trials, and other surgical instruments to prepare the patient's bones to receive the knee prosthesis.

SUMMARY

According to one aspect of the disclosure, an orthopedic surgical instrument assembly includes a broach, a handle, and a depth stop. The broach includes a tapered outer surface extending from a proximal end to a distal end, and a plurality of cutting teeth defined in the outer surface. The handle includes an elongated body that is removably coupled to the distal end of the broach and a plurality of mounting brackets, each mounting bracket being positioned on the elongated body a predetermined distance from a distal surface of the broach. The depth stop includes a mounting bracket configured to be coupled to each mounting bracket of the plurality of mounting brackets of the handle to secure the depth stop to the handle. The depth stop further includes a proximal surface that defines an imaginary plane. A longitudinal axis extends through the proximal end and the distal end of the broach, and when the depth stop is secured to the handle, an oblique angle is defined between the imaginary plane and the axis of the broach. In some embodiments, the oblique angle may have a magnitude of approximately eighty-five degrees.

In some embodiments, each mounting bracket of the handle may include a first slot defined in a first side wall of the elongated body, and the mounting bracket of the depth stop may include a first flange that is configured to be received in the first slot of each mounting bracket. Additionally, in some embodiments, each mounting bracket of the handle may further include a second slot defined in a second side wall of the elongated body, the second slot extending parallel to the first slot, and the mounting bracket of the depth stop may further include a second flange that is spaced apart from the first flange and configured to be received in the second slot of each mounting bracket. In some embodiments, a first channel may be defined between the first flange and the second flange, and the depth stop may further include a first arm, a second arm, and a second channel that is defined between the first arm and the second arm that is sized to receive the elongated body of the handle, the second channel being wider than the first channel. Additionally, in some embodiments, the first arm and the second arm may cooperate to define the proximal surface of the depth stop, and the mounting bracket of the depth stop may be secured to the first arm and the second arm opposite the proximal surface.

In some embodiments, the orthopedic surgical instrument assembly may further include a locking mechanism configured to secure the depth stop to the handle. The locking mechanism may include a latch plate moveable between a locked position in which the latch plate is engaged with the elongated body of the handle and an unlocked position in which the plate is spaced apart from the elongated body. In some embodiments, the locking mechanism may further include a biasing element configured to bias the plate in the locked position. Additionally, in some embodiments, the depth stop may be moveable between a first position in which the mounting bracket of the depth stop is disengaged with a first mounting bracket of the handle and a second position in which the mounting bracket of the depth stop is engaged with the first mounting bracket of the handle. The plate may include a cam surface configured to engage the elongated body to move the plate between the locked position and the unlocked position when the depth stop is moved from the first position to the second position.

In some embodiments, the proximal surface of the depth stop may define a non-captured distal cutting guide. Additionally or alternatively, in some embodiments, the handle may further include a plurality of markings defined on the elongated body, wherein each marking is configured to indicate the predetermined distance associated with one of the plurality of mounting brackets. Additionally, in some embodiments, the surgical instrument assembly may further include a plurality of spacer plates configured to be coupled to the depth stop. Each spacer plate may include a proximal surface that defines a non-captured distal cutting guide and a distal surface configured to engage the proximal surface of the depth stop.

According to another aspect, an orthopedic surgical instrument includes a base plate, a mounting bracket coupled to the base plate, and a locking mechanism configured to secure the orthopedic surgical instrument to a second orthopedic surgical instrument. The base plate includes a first arm, a second arm, and a first channel defined between the first arm and the second arm, the first arm and the second arm defining a non-captured distal cutting guide having a substantially planar proximal surface. The mounting bracket includes a first flange, a second flange, and a second channel defined between the first flange and the second flange. The proximal surface defines an imaginary plane, the second channel defines an axis extending through the imaginary plane, and an oblique angle is defined between the axis and the imaginary plane. In some embodiments, the oblique angle may have a magnitude of approximately eighty-five degrees.

In some embodiments, the locking mechanism may include a latch plate moveably coupled to the mounting bracket and a biasing element. The latch plate may include a catch configured to engage the second orthopedic surgical instrument and a user-operated button operable to move the latch plate between a first position in which the catch is engaged with the second orthopedic surgical instrument and a second position in which the catch is disengaged from the second orthopedic surgical instrument. The biasing element may be configured to bias the latch plate in the first position.

According to another aspect, a method for surgically preparing a distal end of a femur to receive an orthopedic prosthesis is disclosed. The method includes attaching a depth stop to a handle at a first position of a plurality of positions along an elongated body of the handle, securing a broach to an end of the handle, the broach having a tapered outer surface with a plurality of cutting teeth defined in the outer surface, advancing the broach along an anatomical axis of the femur through a distal opening of a medullary canal of the femur, and engaging a proximal surface of the depth stop with a distal surface of the femur, wherein an oblique angle is defined between the proximal surface and the anatomical axis of the femur. In some embodiments, engaging the proximal surface may include engaging the proximal surface such that the oblique angle has a magnitude of approximately eighty-five degrees.

In some embodiments, the method further may include planning a depth of the broach in relation to the distal surface of the femur and selecting the first position of the plurality of positions based on the planned depth of the broach. Engaging the proximal surface may include engaging the proximal surface when the broach is positioned in the medullary canal at the planned depth. In some embodiments, planning the depth of the broach may include planning the depth based on a size of the orthopedic prosthesis to be implanted.

In some embodiments, the method may further include engaging a non-captured cutting guide of the proximal surface of the depth stop to resect the distal end of the femur, advancing the broach along an anatomical axis of the femur after resecting the distal end, and engaging the proximal surface of the depth stop with the distal surface of the femur after resecting the distal end. Additionally, in some embodiments, the method may further include planning a depth of the broach in relation to the distal surface of the femur, selecting a spacer plate from a plurality of spacer plates based on the planned depth, the spacer plate having a proximal surface that defines a non-captured distal cutting guide, and attaching the spacer plate to the depth stop such that the proximal surface of the spacer plate is the proximal surface of the depth stop.

BRIEF DESCRIPTION OF THE DRAWINGS

The detailed description particularly refers to the following figures, in which:

FIGS. 11-16 are views of a patient's femur and the orthopedic surgical instrument assembly of FIGS. 1-10 during the performance of an orthopedic surgical procedure.

DETAILED DESCRIPTION OF THE DRAWINGS

Figure 1:
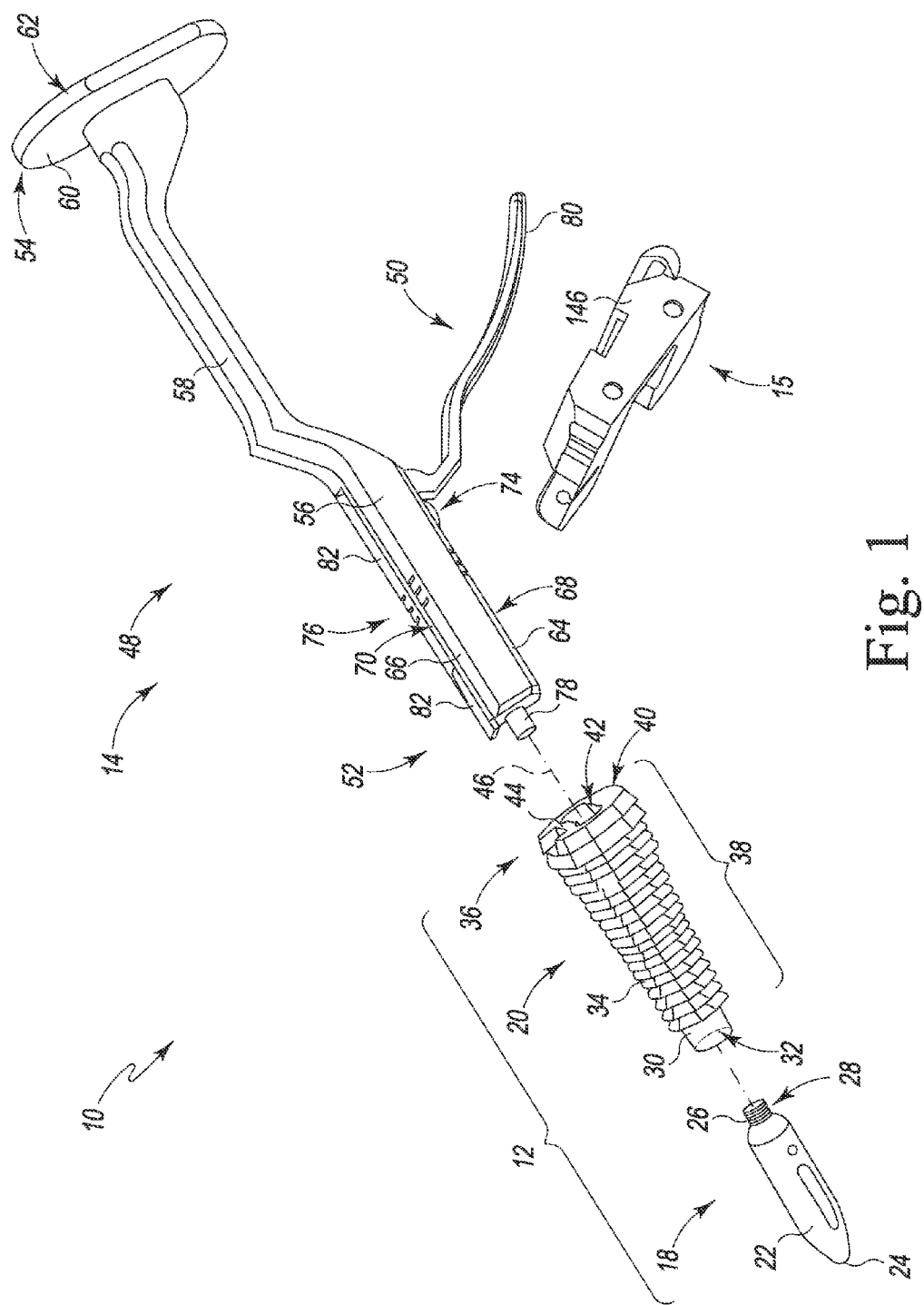
FIG. 1 is an exploded perspective view of an orthopedic surgical instrument assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopedic implants and orthopedic surgical instruments described herein as well as in reference to the patient's natural anatomy. Such terms have well-understood meanings in both the study of anatomy and the field of orthopedics. Use of such anatomical reference terms in the written description and claims is intended to be consistent with their well-understood meanings unless noted otherwise.

Referring now to FIG. 1, an orthopedic surgical instrument assembly 10 (hereinafter instrument assembly 10) is shown. As used herein, the terms "orthopedic surgical instrument" or "orthopedic surgical instrument assembly" refer to surgical tools used by a surgeon in performing an orthopedic surgical procedure. As such, it should be appreciated that, as used herein, the terms "orthopedic surgical instrument" and "orthopedic surgical instruments" are distinct from orthopedic implants or prostheses that are surgically implanted in the body of the patient.

The instrument assembly 10 includes an intramedullary surgical instrument 12, an orthopedic surgical instrument handle 14 configured to be secured to the intramedullary surgical instrument 12, and a depth stop 16 configured to be secured to the instrument handle 14. As described in greater detail below, the surgeon may use the instrument handle 14 and the depth stop 16 to sequentially advance the intramedullary surgical instrument 12 into the medullary canal of the patient's femur to prepare the femur to receive a femoral prosthetic component. The surgeon may also use the depth stop 16 to resect the distal end of the patient's femur. Although the illustrative instrument assembly 10 is used to prepare the femur, other embodiments of the instrument assembly 10 may be used to prepare other bones or joints, for example the proximal end of the patient's tibia.

The intramedullary surgical instrument 12 includes a femoral stem trial 18 coupled to a broach 20. It should be appreciated that in other embodiments the intramedullary surgical instrument 12 may take other forms. For example, the stem trial 18 and/or the broach 20 may be substituted for different sized instruments or different configurations. Additionally, in other embodiments, the intramedullary surgical instrument 12 may include a femoral stem trial without a broach, or may include another surgical instrument such as a stem stabilizer.

As shown in FIG. 1, the stem trial 18 of the intramedullary surgical instrument 12 has an elongated body 22 that extends from a proximal tip 24 to a distal end 26. The distal end 26 has a plurality of external threads 28 formed thereon. It should be appreciated that other stem trials having different configurations may be provided. For example, the outer diameter and/or length of the stem trial may vary to trial prosthetic components of different sizes.

The broach 20 of the intramedullary surgical instrument 12 includes a proximal tip 30 and an outer surface 34 extending from the proximal tip 30 to a distal end 36. The tip 30 of the broach 20 includes an aperture 32 defined therein that is sized to receive the threaded distal end 26 of the femoral stem trial 18. An inner wall defines the aperture 32, and the inner wall may have a plurality of internal threads formed thereon that correspond to the external threads 28 of the distal end 26 of the stem trial 18. The aperture 32 and the internal threads thereby may secure the stem trial 18 to the broach 20.

The outer surface 34 of the broach 20 is tapered, with the cross-sectional area of the broach 20 increasing from the tip 30 to the distal end 36. A plurality of cutting teeth 38 are formed on the outer surface 34 between the tip 30 and the distal end 36. As described in greater detail below, the cutting teeth 38 are configured to engage the bone surrounding the medullary canal of the patient's femur when the broach 20 is inserted therein. It should be appreciated that other broaches 20 having different configurations may be provided. For example, the outer diameter and/or length of the broach may vary to produce different sized canals to accommodate prosthetic components of different sizes.

The broach 20 includes a substantially planar distal surface 40 positioned at the distal end 36. A central aperture 42 is defined in the distal surface 40. The central aperture 42 is sized to receive a guide pin 78 of the instrument handle 14, as described in greater detail below. The broach 20 also includes a flange 44 positioned adjacent to the central aperture 42, which is engaged by an attachment mechanism 50 of the instrument handle 14. As described below, a longitudinal axis 46 of the broach extends through the tip 30 and the central aperture 42. The axis 46 may be aligned with the anatomical axis of the patient's femur when the broach 20 is inserted in the medullary canal, as described in detail below.

As shown in FIG. 1, the instrument handle 14 includes an elongated tool body 48 and an attachment mechanism 50. The attachment mechanism 50 is configured to secure the intramedullary surgical instrument 12 to the instrument handle 14, as described in detail below. The tool body 48 extends from a proximal end 52 to a distal end 54. In the illustrative embodiment, the tool body 48 is formed from metallic material, such as, for example, stainless steel or cobalt chromium. The tool body 48 includes a housing 56 positioned at the proximal end 52 and a grip 58 positioned distal of the housing 56. The grip 58 is configured receive the hand of a surgeon or other user to allow the user to manipulate the instrument handle 14. Accordingly, the grip 58 may be coated in a rubberized or textured material to improve grip stability. In some embodiments, the grip 58 may be formed as a separate unit from the housing 56 and assembled with the housing 56 to form the tool body 48.

The instrument handle 14 further includes an impaction plate 60 attached to the grip 58 at the distal end 54 of the tool body 48. The impaction plate 60 is securely attached to the rest of the instrument handle 14, for example by mechanically threading onto the end of the grip 58. The impaction plate 60 includes a durable distal surface 62 suitable for use with a striking tool such as a mallet, sledge, or other impaction tool. The distal surface 62 is large enough to cover the grip 58 in order to shield the hand of the user. In use, the surgeon may impact the impaction plate 60 to advance the intramedullary surgical instrument 12 into the medullary canal of the patient's femur.

The housing 56 of the instrument handle 14 further includes a pair of side surfaces 64, 66 extending from the proximal end 52 to the grip 58. A pair of openings 68, 70 are defined in the side surfaces 64, 66. A number of inner walls 72 extend between the openings 68, 70 through the housing 56. The inner walls 72 define a cavity 74 inside the housing 56. As described in detail below, the cavity 74 contains components of the attachment mechanism 50. A number of mounting brackets 76 defined in the side surfaces 64, 66. The mounting brackets 76 are configured to separately engage a mounting bracket 146 of the depth stop 16.

As described above, the instrument handle 12 includes a guide pin 78 that is configured to be received by the intramedullary surgical instrument 12. The guide pin 78 extends from the proximal end 52 of the instrument handle 12. The attachment mechanism 50 of the instrument handle 14 includes the guide pin 78, a user-operated release lever 80 extending distally out of the cavity 74 through the opening 68, and a clamp lever 82 extending outwardly through the opening 70 toward the guide pin 78. When the release lever 80 is moved by the user from an unclamped position to a clamped position, the clamp lever 82 engages the flange 44 of the broach 20 to secure the intramedullary surgical instrument 12 to the instrument handle 14 as described below.

Figure 2:
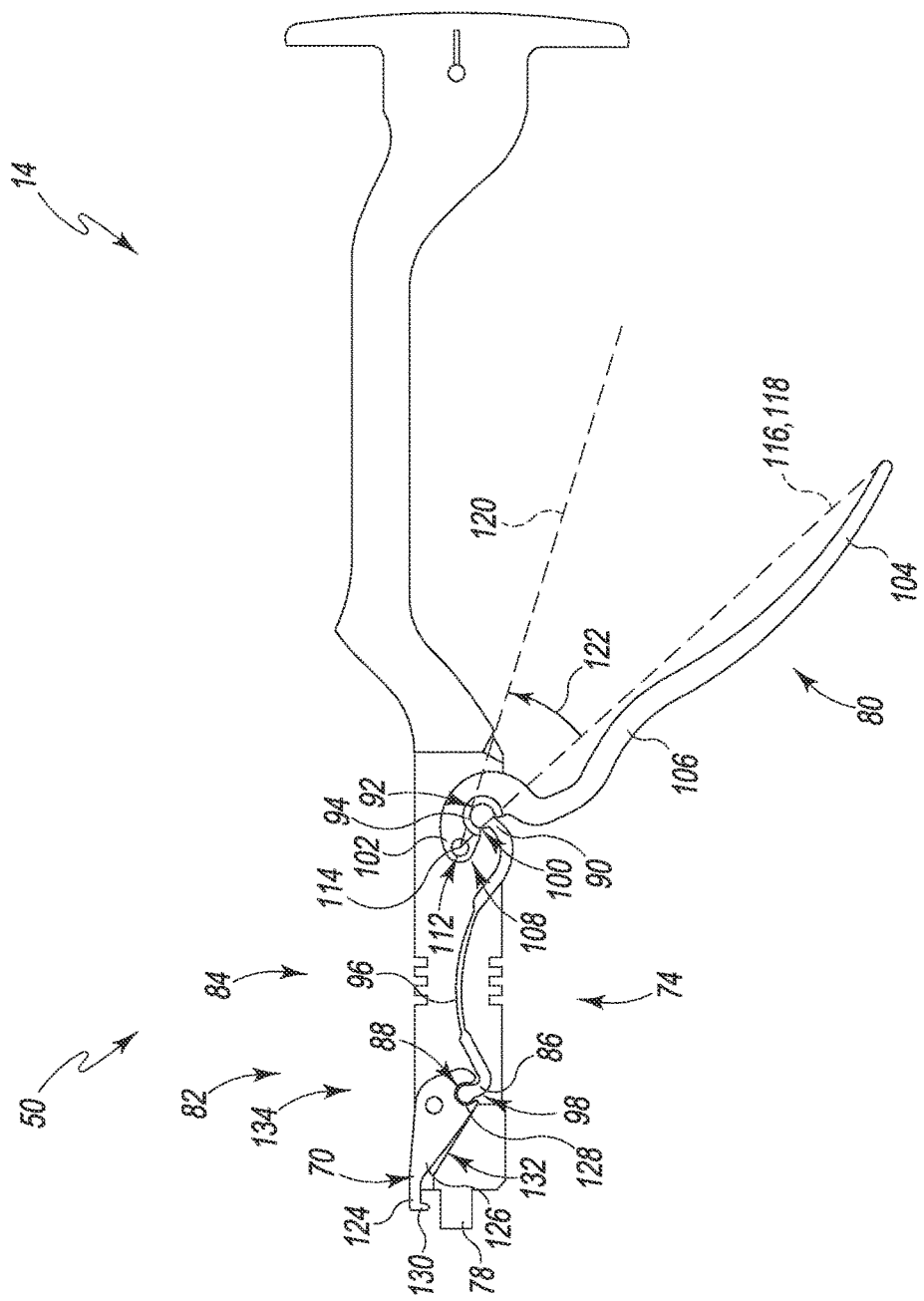
FIG. 2 is a cross-sectional elevation view of an orthopedic instrument handle of the instrument assembly of FIG. 1 showing an operating lever in one position.
Figure 3:
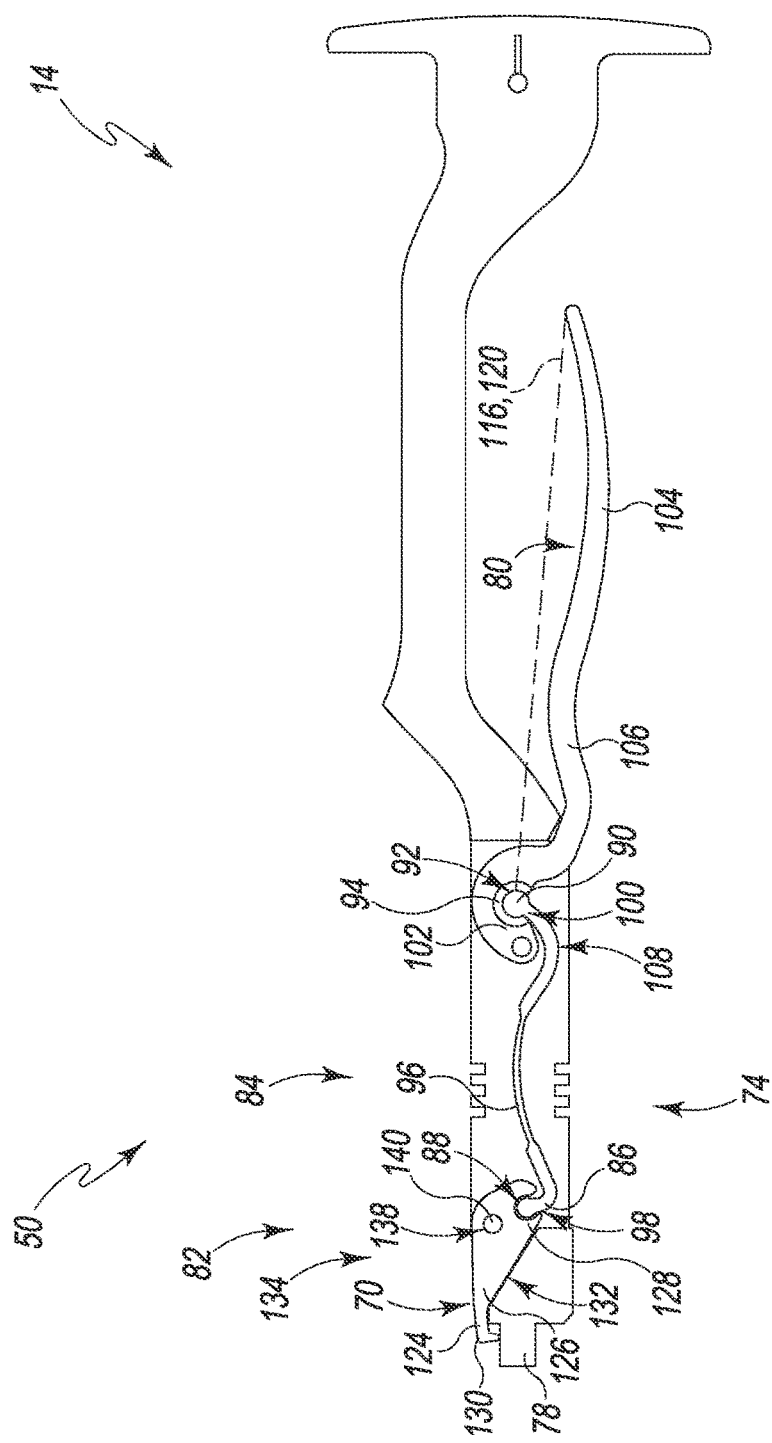
FIG. 3 is a view similar to FIG. 2 showing the operating lever in another position.

Referring now to FIGS. 2 and 3, the attachment mechanism 50 of the instrument handle 14 further includes a leaf spring 84 that is coupled between the release lever 80 and the clamp lever 82. The leaf spring 84 includes a circular tip 86 positioned at the proximal end that is coupled to a complementarily shaped circular slot 88 defined in the clamp lever 82. The leaf spring 84 further includes a circular tip 90 positioned at the distal end that is coupled to a complementarily shaped circular slot 92 defined in the release lever 80. The tips 86, 90 may rotate within the slots 88, 92, pivotally coupling the leaf spring 84 to the release lever 80 and the clamp lever 82.

The slot 92 includes an insert 94 configured to facilitate rotation of the tip 90 within the slot 92. The insert 94 may be formed from a low-friction polymeric material. The leaf spring 84 has a flexible body 96 positioned between the tips 86, 90. The slots 88, 92 include openings 98, 100, respectively, through which the flexible body exits the slots 88, 92. Each tip 86, 90 has a diameter larger than the respective opening 98, 100 thereby mechanically securing the tips 86, 90 within the slots 88, 92. Each tip 86, 90 may be formed from thicker material, be less flexible, and be more durable than the flexible body.

The release lever 80 includes a proximal end 102 that is pivotally coupled to the tool body 48, a distal end including a grip 104, and a lever body 106 coupled between the proximal end 102 and the grip 104. The grip 104 is configured to be gripped by the surgeon or other user when moving the release lever 80 between the unclamped position and the clamped position. The slot 92 is positioned in the lever body 106 between the proximal end 102 and the grip 104, thereby providing mechanical advantage.

The proximal end 102 of the release lever 80 is pivotally coupled to the tool body 48 via a joint 108. The joint 108 includes circular openings 110 extending through the housing 56 and a bore 112 defined in the release lever 80. The bore 112 encompasses the pivot point of the release lever 80. A cylindrical cross-pin 114 is positioned in the openings 110 and the bore 112 such that the release lever 80 is joined with the tool body 48. In the illustrative embodiment, the cross-pin 114 is press-fit to the opening 110, however, any suitable method of securing the cross-pin 114 may be used.

The release lever 80 includes a longitudinal axis 116 extending between the proximal end 102 and the grip 104. Referring to FIG. 2, the longitudinal axis 116 is illustrated in the unclamped position 118 and the clamped position 120. An angle 122 is defined between the longitudinal axis in the unclamped position 118 and the longitudinal axis in the clamped position 120. The angle 122 is the throw of the release lever 80, that is, the angle 122 represents the distance the surgeon must move the release lever 80 to fully engage the clamp lever 82. The angle 122 may have a magnitude of about eighty degrees.

The clamp lever 82 has a roughly triangular, non-linear shape. The clamp lever 82 includes an arm 124 extending out of the opening 70 toward the guide pin 78, and a shoulder 126 extending distally from the arm 124 toward a distal end 128 positioned within the cavity 74. The arm 124 includes a catch 130 configured to engage the flange 44 of the broach 20 and thereby secure the broach 20 when the release lever 80 is in the clamped position (see FIG. 3). As described above, the clamp lever 82 is moveable between an unclamped position (see FIG. 2) and a clamped position (see FIG. 3). When in the unclamped position, the arm 124 is spaced apart from the guide pin 78. When the clamp lever 82 is moved from the unclamped position to the clamped position, the arm 124 moves closer to the guide pin 78 and engages the flange 44. Additionally, when in the clamped position, the shoulder 126 of the clamp lever 82 may engage an angled inner wall 132 of the cavity 74. The inner wall 132 thus may operate as a stop for the motion of the clamp lever 82. The distal end 128 of the clamp lever 82 is pivotally coupled to the tool body 48. The slot 88 is defined in the distal end 128.

The clamp lever 82 is pivotally coupled to the tool body 48 via a joint 134. The joint 134 includes a circular opening 136 extending through the housing 56 and a bore 138 defined in the clamp lever 82. The bore 138 encompasses the pivot point for the clamp lever 82. It should be noted that the arm 124, the bore 138, and the slot 88 do not lie on a common line. A cylindrical cross-pin 140 is positioned in the opening 136 and the bore 138 such that the clamp lever 82 is joined with the tool body 48. In the illustrative embodiment, the cross-pin 140 is press-fit to the opening 136, however, any suitable method of securing the cross-pin 140 may be used.

When the release lever 80 is in the extended, or unclamped position illustrated in FIG. 2, the clamp lever 82 is spaced apart from the guide pin 78. Additionally, the leaf spring 84 has a relaxed, arcuate shape. When the release lever 80 is moved to the clamped position as shown in FIG. 3, the leaf spring 84 has an extended and relatively flattened shape, causing the leaf spring 84 to be in tension. The leaf spring 84 causes the clamp lever 82 to move toward the guide pin 78, securing the intramedullary surgical instrument 12 to the instrument handle 14. Once in tension, the leaf spring 84 pulls the clamp lever 82 toward the distal end 54 of the tool body 48 and biases the release lever 80 and the clamp lever 82 to remain in the clamped position. The intramedullary surgical instrument 12 may be released by moving the release lever 80 from the clamped to the unclamped position.

Figure 4:
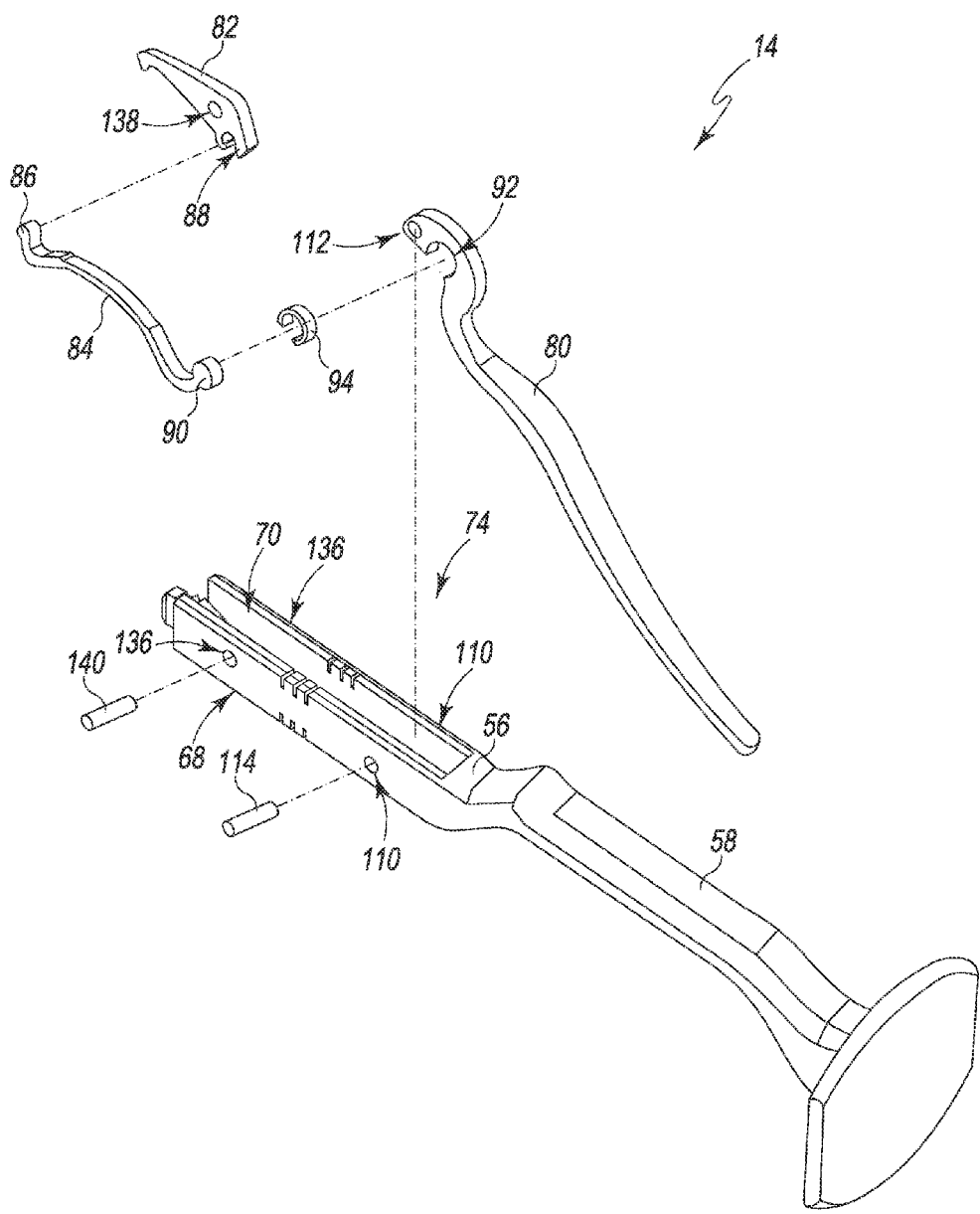
FIG. 4 is an exploded perspective view of the instrument handle of FIGS. 1-3.

Referring now to FIG. 4, the instrument handle 14 may be assembled from component parts by inserting the tip 86 of the leaf spring 84 into the slot 88 of the clamp lever 82. The insert 94 may be inserted into the slot 92 of the release lever 80. The tip 90 of the leaf spring 84 may be inserted into the slot 92 of the release lever 80. The assembled clamp lever 82, leaf spring 84, and release lever 80 may be inserted into the cavity 74 of the housing 56 through one of the openings 68, 70. The clamp lever 82 may be pivotally secured to the tool body 48 by inserting the cross-pin 140 through the bore 138 and the openings 136. The release lever 80 may also be pivotally secured to the tool body 48 by inserting the cross-pin 114 through the bore 112 and the openings 110.

Figure 5:
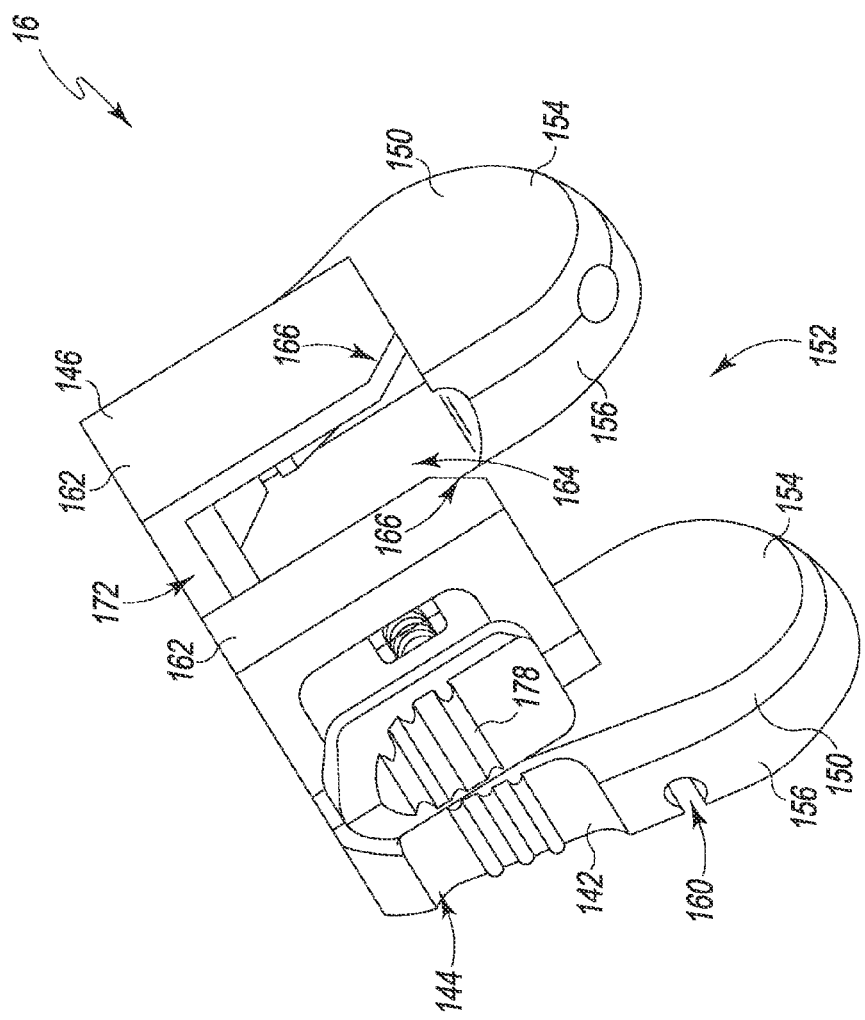
FIG. 5 is a perspective view of a depth stop of the instrument assembly of FIG. 1.
Figure 6:
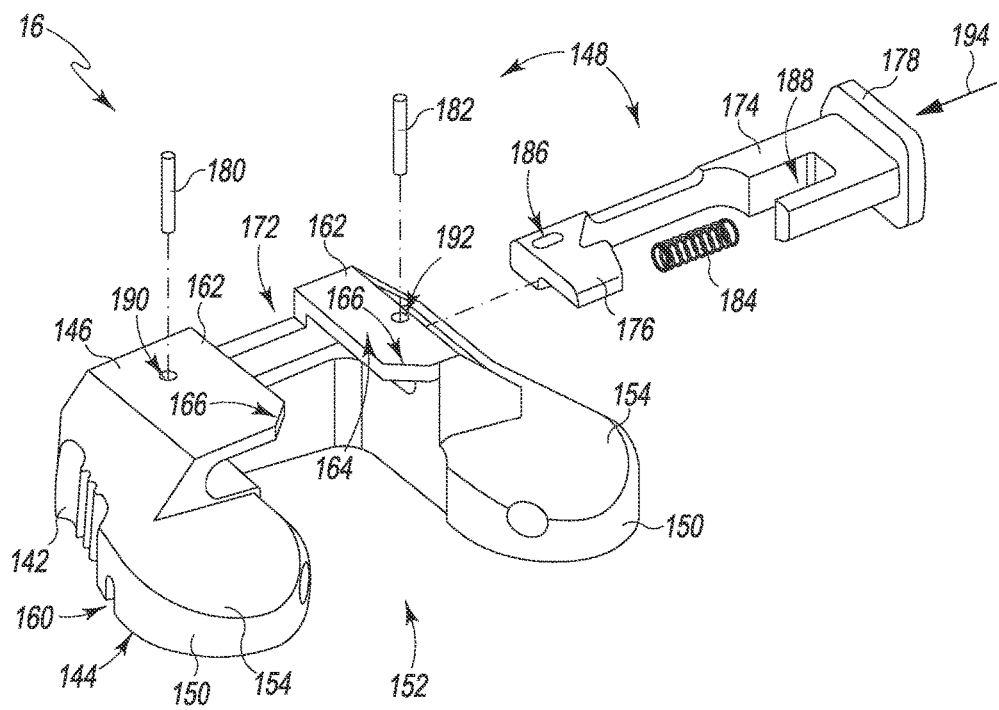
FIG. 6 is an exploded perspective view of the depth stop of FIG. 5.
Figure 7:
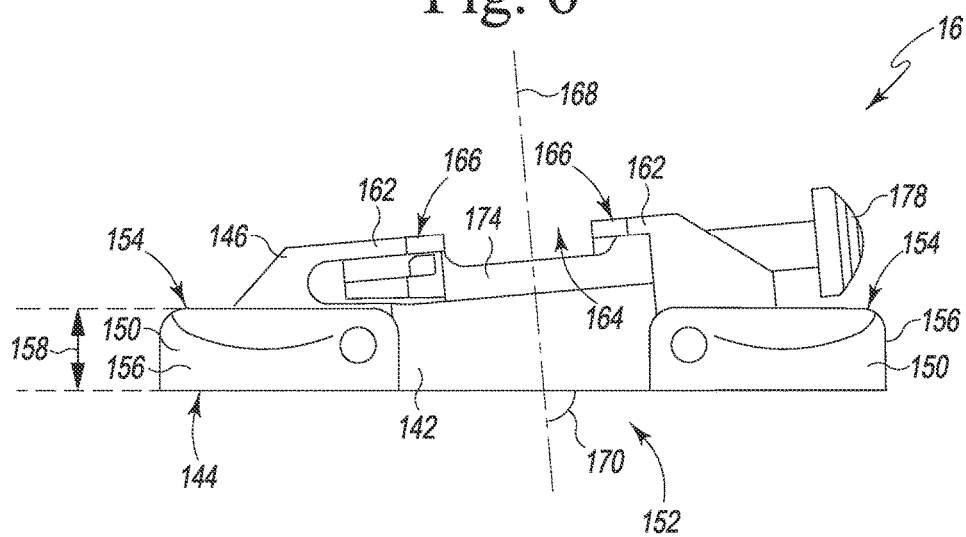
FIG. 7 is a bottom plan view of the depth stop of FIGS. 5-6.

Referring now to FIGS. 5-7, the depth stop 16 includes a base plate 142 that defines a substantially planar proximal surface 144 that may be used by the surgeon to seat the intramedullary surgical instrument 12 at the proper depth in the patient's medullary canal. The depth stop 16 also includes a mounting bracket 146 coupled to the base plate 142. The mounting bracket 146 is configured to engage one of the mounting brackets 76 of the instrument handle 14, as mentioned above. The depth stop 16 additionally includes a locking mechanism 148 that is configured to secure the instrument handle 14 to the depth stop 16, as described in greater detail below.

The base plate 142 of the depth stop 16 includes a pair of arms 150 that cooperate to define the proximal surface 144 of the depth stop 16. A channel 152 extending through the proximal surface 144 is defined between the arms 150 and is sized to receive the housing 56 of the instrument handle 14. In the illustrative embodiment, the proximal surface 144 may be used by the surgeon as a non-captured distal cutting guide to resect the distal end of the femur, as described in more detail below.

The base plate 142 includes a distal surface 154 positioned opposite the proximal surface 144. The distal surface 154 and the proximal surface 144 are separated by a wall 156 having a maximum thickness 158. In some embodiments, the thickness 158 may be equivalent to the thickness of a prosthetic femoral component to be installed. In some embodiments, the thickness 158 may be approximately nine millimeters.

Each of the arms 150 may include a cylindrical passageway 160 extending parallel to the proximal surface 144. The passageways 160 are configured to secure additional surgical instruments to the depth stop 16 such as a modular cutting guide or a measurement gauge, as described below. The passageways 160 may be partially exposed through the proximal surface 144 as illustrated (see FIG. 5), or in some embodiments may be fully contained within the arms 150.

The mounting bracket 146 of the depth stop 16 is secured to the base plate 142 opposite the proximal surface 144. The mounting bracket 146 includes a pair of flanges 162 configured to engage each of the mounting brackets 76 of the instrument handle 14. A channel 164 is defined between the flanges 162 that is more narrow than the channel 152 defined by the arms 150. Thus, the flanges 162 stabilize the depth stop 16 by engaging the corresponding one of the mounting brackets 76. A corner of each flange 162 includes a chamfer 166 to allow the depth stop 16 to slide onto the instrument handle 14 more readily. Although illustrated as including a pair of flanges 162, in some embodiments the mounting bracket 146 may include a single flange, lug, or other projection configured to be received by each of the mounting brackets 76 of the instrument handle 14.

The channels 152, 164 further define an axis 168 that intersects the proximal surface 144 (see FIG. 7). The axis 168 and the proximal surface 144 define an oblique angle 170; that is, the axis 168 is not perpendicular to the proximal surface 144. In use, the oblique angle 170 accounts for the angle between the anatomical axis of the patient's femur and the joint line between the femoral component and the polymer bearing of the prosthetic knee joint. The magnitude of the angle 170 matches the prosthetic component; in other words, the angle 170 corresponds to the angle between the distal surface of the femoral component and the anatomical axis. In some embodiments, the angle 170 may have a magnitude of approximately 85 degrees. Further, the angle 170 extends outward laterally for both right-handed and left-handed knees. Therefore, a specialized depth stop 16 may be used for either the right-hand knee or the left-hand knee.

The mounting bracket 146 further includes a notch 172 configured to allow any markings on the instrument handle 14 associated with the engaged mounting bracket 76 to be visible when the depth stop 16 is attached to the instrument handle 14.

Referring now to FIG. 6, the depth stop 16 further includes the locking mechanism 148, which is configured to secure the depth stop 16 to the instrument handle 14. The locking mechanism 148 includes a latch plate 174 configured to slide within the mounting bracket 146, a pair of pins 180, 182 configured to secure the latch plate 174 to the mounting bracket 146, and a biasing element 184. The latch plate 174 includes a catch 176 positioned on one end that is configured to engage the instrument handle 14. On the other end, the latch plate 174 includes a user-operated button 178 that is operable to selectively engage or disengage the catch 176. In the illustrative embodiment, the button 178 includes a contoured outer surface that is configured to receive a fingertip of a surgeon or other user. The latch plate 174 further includes an elongated opening 186 defined near the catch 176, and an aperture 188 defined near the button 178.

The pin 180 is positioned within the elongated opening 186 of the latch plate 174 and a bore 190 defined in the mounting bracket 146. Thus, the elongated opening 186 defines the range of travel for the latch plate 174. The pin 182 is positioned within the aperture 188 and a bore 192 defined in the mounting bracket 146. The biasing element 184, in the illustrative example a spring, is positioned between the latch plate 174 and the pin 182. The biasing element 184 presses against the latch plate 174 and biases the catch 176 in the engaged position shown in FIG. 7. When the button 178 is pressed in a direction indicated by the arrow 194, the latch plate 174 moves to a disengaged position. The latch plate 174 further includes a cam surface 196 positioned on the catch 176.

Figure 8:
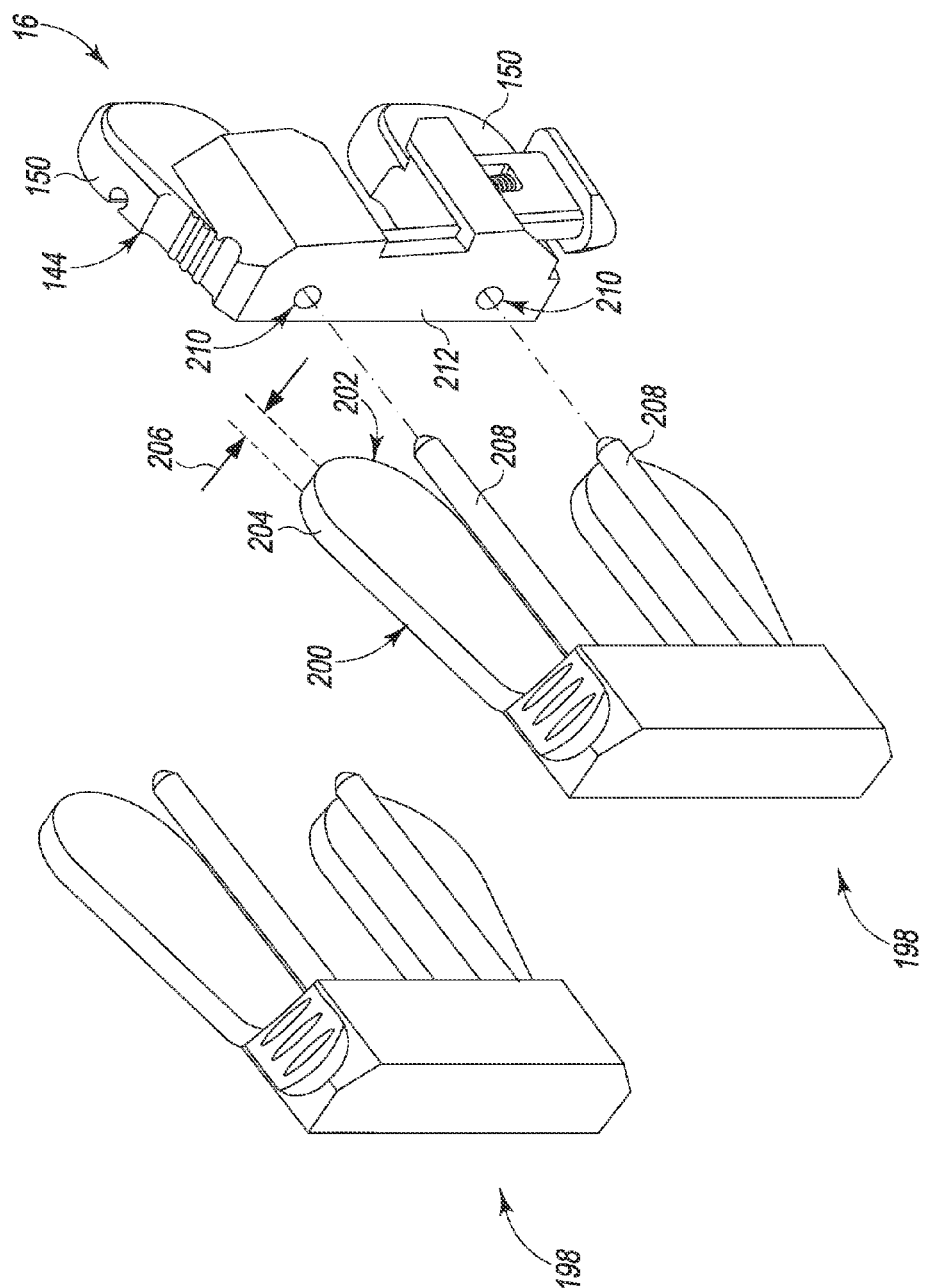
FIG. 8 is a perspective view of a group of a plurality of spacer plates for use with the broach stop of FIGS. 5-7.

Referring now to FIG. 8, the instrument assembly 10 may be used with a number of spacer plates 198 that each may be attached to the depth stop 16. Each of the spacer plates 198 includes a substantially planar proximal surface 200 opposite a distal surface 202. The proximal surface 200 and the distal surface 202 are separated by a wall 204 having a thickness 206.

Each of the spacer plates 198 further includes a pair of pins 208 that are used to secure the plate to the depth stop 16. The depth stop 16 includes a pair of mounting holes 210 defined in a substantially planar wall 212 connecting the proximal surface 144 and the mounting bracket 146. The mounting holes 210 extend from the wall 212 through the arms 150 parallel to the proximal surface 144. The pins 208 of each of the spacer plates 198 may slide into the mounting holes 210, securing the spacer plate 198 to the depth stop 16. When the spacer plate 198 is secured to the depth stop 16, the distal surface 202 engages the proximal surface 144 of the depth stop 16. In some embodiments, one or more additional or different attachment devices may be secured to the depth stop 16 using the mounting holes 210, for example a mounting bracket for a captured cutting block or mounting pins of a captured cutting block. In some embodiments, a captured cutting block may be attached to similar mounting holes of the spacer plate 198 (not shown).

When the spacer plate 198 is secured to the depth stop 16, the surgeon may use the proximal surface 200 of the spacer plate 198 as a non-captured distal cutting guide, as described in greater detail below. Each of the spacer plates 198 may have a different thickness 206, allowing the surgeon to select an appropriate cutting depth. For example, spacer plates 198 may be embodied with thicknesses 206 of 4 millimeters, 8 millimeters, 12 millimeters, and 16 millimeters. Thus, when a spacer plate 198 is attached to the depth stop 16, the position of the proximal surface 144 is effectively moved closer to the distal end of the broach 20 by the thickness 206 of the spacer plate 198.

Figure 9:
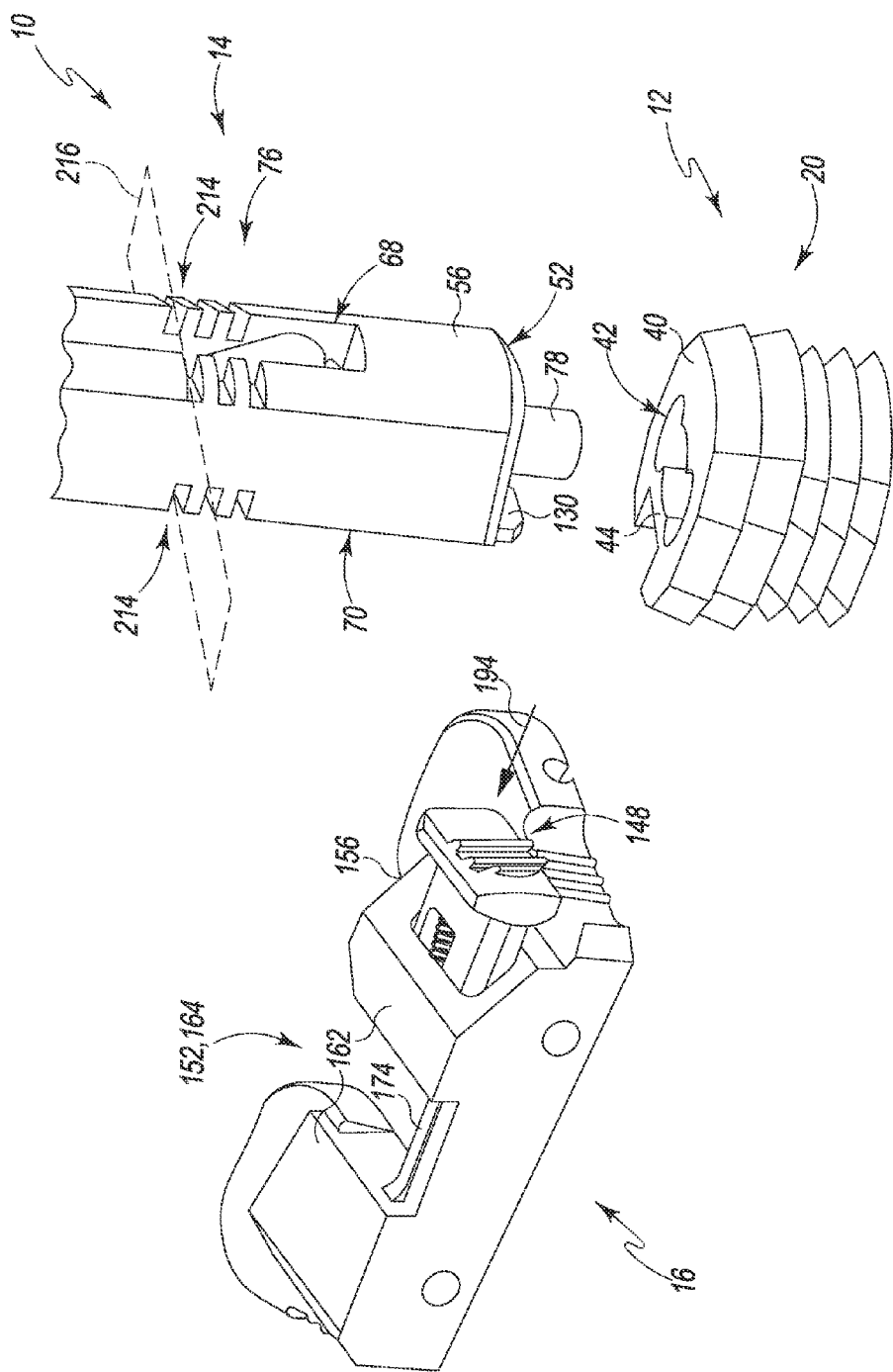
FIG. 9 is an exploded fragmentary perspective view of the orthopedic surgical instrument assembly of FIG. 1.

Referring now to FIG. 9, the depth stop 16 may be attached to the instrument handle 14 by aligning the channels 152, 164 of the depth stop 16 with the mounting brackets 76 of the instrument handle 14. Each mounting bracket 76 may be embodied as a pair of slots 214 defined in the side surfaces 64, 66 extending transversely across the openings 68, 70. Each pair of slots 214 may be positioned on a common imaginary plane 216. The flanges 162 of the depth stop 16 are aligned with one of the pairs of slots 214. It should be noted that in some embodiments, rather than as the pairs of slots 214, each of the mounting brackets 76 may be embodied as a single recess formed in the exterior of the tool body 48 that is configured to receive the mounting bracket 146 of the depth stop 16. The depth stop 16 may then be brought into contact with the instrument handle 14.

As the depth stop 16 is brought into contact with the instrument handle 14, the flanges 162 engage the selected one of the pairs of slots 214. As the depth stop 16 further engages the instrument handle 14, the flanges 162 slide along the selected pair of slots 214, and the cam surface 196 of the locking mechanism 148 is advanced into contact with the housing 56 of the instrument handle 14. The engagement of the cam surface 196 and the housing 56 causes the latch plate 174 to move in the direction indicated by the arrow 194 to disengage the catch 176. As the flanges 162 slide further along the selected pair of slots 214, the cam surface 196 disengages, allowing the spring 184 to urge the catch 176 to return to the engaged position, thereby securing the depth stop 16 to the instrument handle 14. The flanges 162 slide along the selected pair of slots 214 until the housing 56 contacts the wall 156 of the depth stop 16 positioned at the end of the channel 164.

The intramedullary surgical instrument 12 may be attached to the instrument handle 14 by aligning the central aperture 42 of the broach 20 with the guide pin 78 of the instrument handle 14, and the flange 44 of the broach 20 with the catch 130 of the instrument handle 14. The instrument handle 14 is advanced with the release lever 80 in the unlocked position, moving the guide pin 78 into the central aperture 42 until the proximal end 52 of the tool body 48 engages the distal surface 40 of the broach 20. The grip 58 and the release lever 80 of the instrument handle 14 are squeezed together to move the release lever 80 to the clamped position, and the catch 130 engages the flange 44, thereby securing the broach 20 to the instrument handle 14. When the release lever 80 is in the clamped position, the leaf spring 84 provides clamping force to secure the intramedullary surgical instrument 12 to the instrument handle 14.

Figure 10:
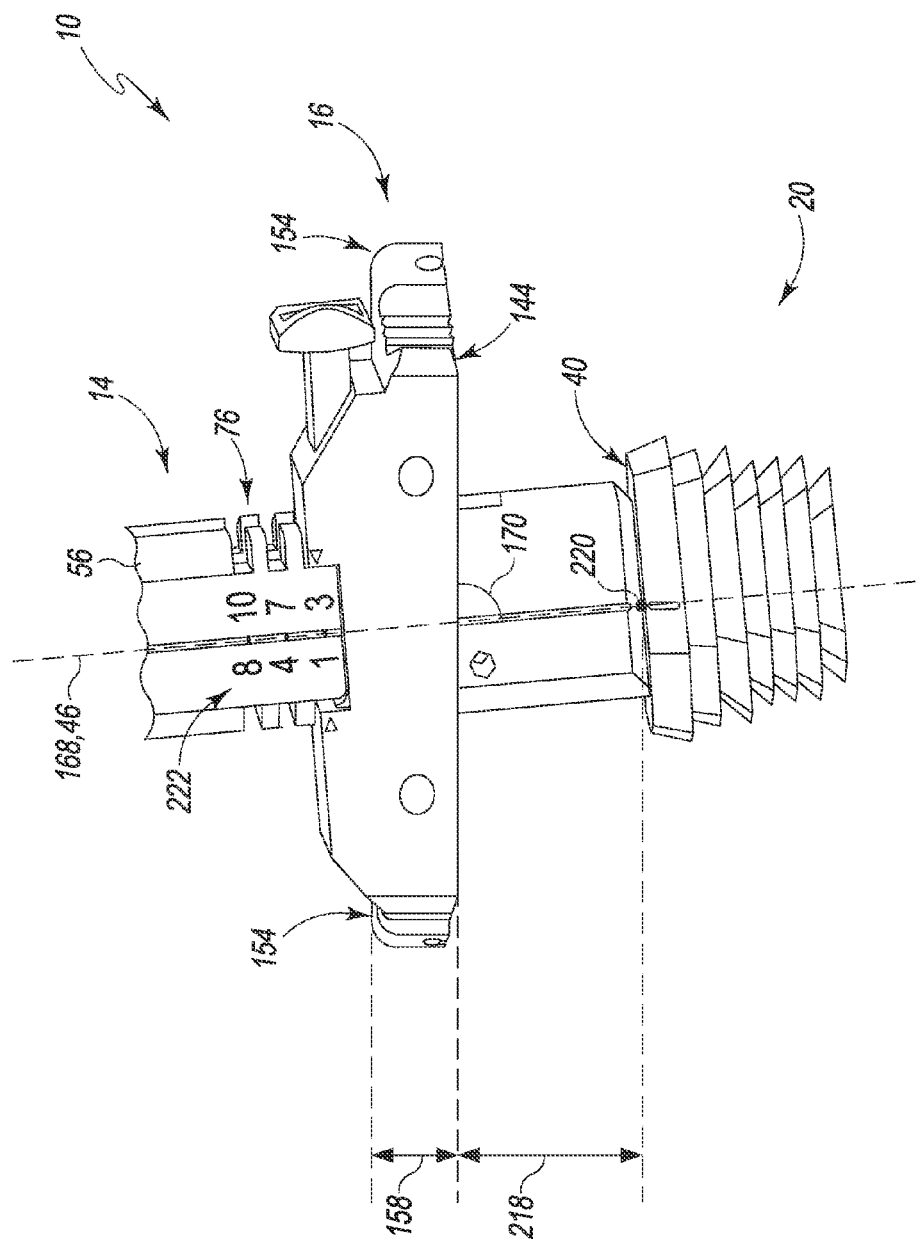
FIG. 10 is a fragmentary elevation view of the instrument assembly of FIG. 1.

Referring now to FIG. 10, as described above, the angle 170 is defined by the proximal surface 144 and the axis 168 that is defined by the channels 152, 164 of the depth stop 16. The angle 170 is also defined by broach axis 46 and the proximal surface 144 when the instrument assembly 10 is assembled, because when properly assembled the broach axis 46 and the axis 168 coincide. Also as described above, the angle 170 may have a magnitude of about eighty-five degrees.

Further, when the instrument assembly 10 is assembled, a distance 218 is defined between the distal surface 40 of the broach 20 and the proximal surface 144 of the depth stop 16. Because the angle 170 causes such distance 218 to vary over the extent of the proximal surface 144, the distance 218 may be defined as the shortest distance between a point 220 on the distal surface 40 of the broach 20 that intersects the broach axis 46 and the proximal surface 144. The distal surface 154 of the depth stop 16 is positioned further away from the distal surface 40 of the broach 20 by the thickness 158, which is constant over the extent of the proximal surface 144.

Each of the mounting brackets 76 is associated with a predetermined distance 218 between the proximal surface 144 and the distal surface 40 of the broach 20. Thus, the surgeon may select the mounting bracket 76 for attachment based on the desired distance 218. A set of markings 222 on the housing 56 may assist the surgeon in selecting the mounting bracket 76. The markings 222 are visible through the notch 172 of the depth stop 16. It should be noted that in other embodiments, rather than including several mounting brackets 76, the instrument handle 14 may include a single mounting bracket 76. In that example, the instrument assembly 10 includes a number of depth stops 16, each having a different thickness 158. Accordingly, in that example the distance 218 depends on the selected depth stop 16.

The instrument assembly 10 may be utilized during the performance of an orthopedic surgical procedure similar to that shown in FIGS. 11-16. As shown in FIGS. 11-15, the surgeon may initially prepare the medullary canal. The surgeon may then assemble the instrument assembly 10 and insert the intramedullary surgical instrument 12 into the medullary canal. As shown in FIG. 16, the surgeon may resect the distal surface of the femur as necessary. As shown in FIG. 16, the surgeon may attach additional orthopedic instruments to the broach 20 to further prepare the distal surface of the femur.

Figure 11:
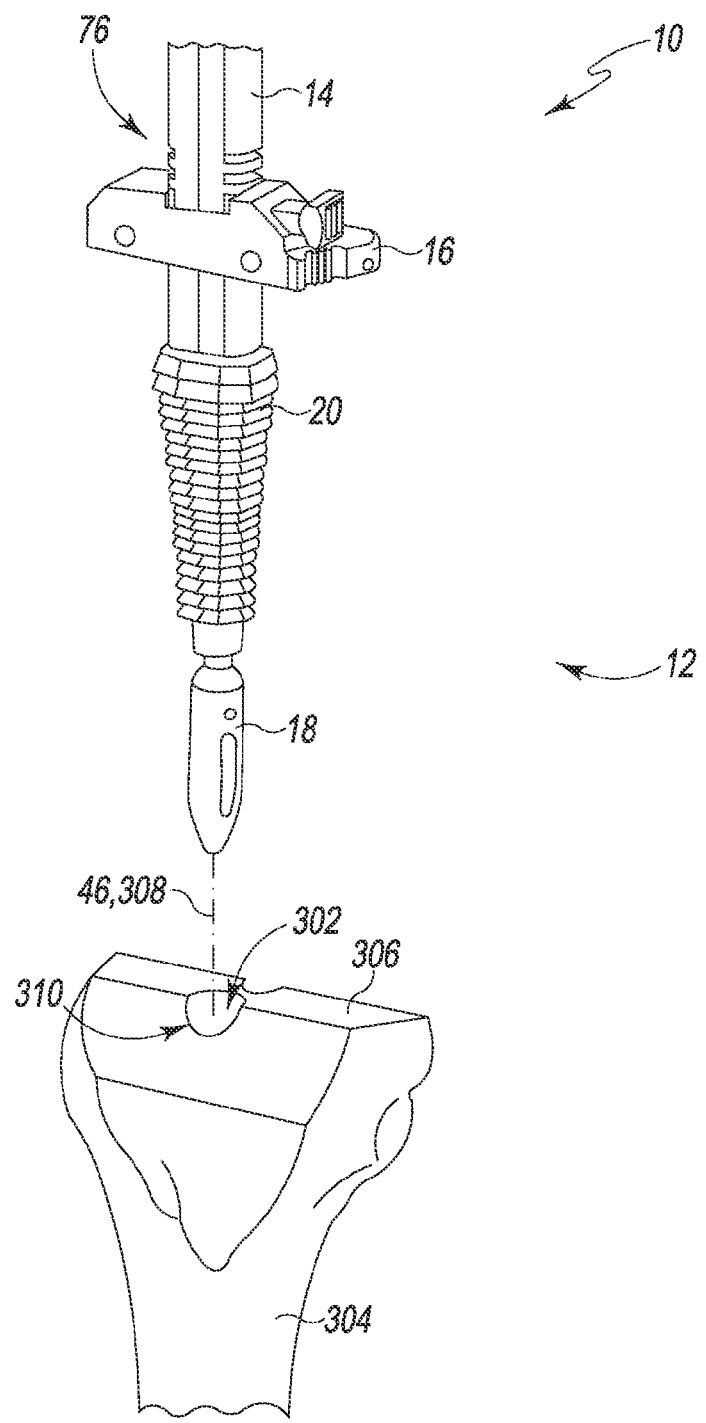

The surgeon initially prepares the medullary canal 302 of the patient's femur 304. To do so, the surgeon may insert an initial surgical reamer into the medullary canal 302. In some embodiments, the threaded distal end 26 of the stem trial 18 may be secured to the reamer prior to insertion in the medullary canal 302. The surgeon may use the reamer to drill and/or ream the medullary canal 302 to the depth and/or diameter required to receive the broach 20 and/or the stem trial 18. Multiple drills or reamers may be used to increase the size of the opening of the medullary canal formed on the distal end of the patient's femur. When the reaming operation is complete, the medullary canal 302 is configured as shown in FIG. 11 and is ready to receive the intramedullary surgical instrument 12.

After preparing the medullary canal 302, the surgeon assembles the instrument assembly 10 by attaching the depth stop 16 and the intramedullary surgical instrument 12 to the instrument handle 14 as described above. As described above, the surgeon may select a depth stop 16 specialized for either the right-hand knee or the left-hand knee. Before assembly, the surgeon may plan the final depth of the intramedullary surgical instrument 12 in relation to a distal surface 306 of the patient's femur 304. The depth depends on the size of prosthetic femoral component to be installed. The depth may also depend on the condition of the distal surface 306 of the patient's femur 304. The surgeon may make this determination pre-operatively or intraoperatively, depending on the condition of the patient's femur 304. For example, if large amounts of bone are deteriorated or missing, the surgeon may select a shallower final depth, that is, the surgeon may distalize the position of the broach 20.

Based on the planned final depth of the intramedullary surgical instrument 12, the surgeon selects a mounting bracket 76 located in an appropriate position on the instrument handle 14 and attaches the depth stop 16 to that selected mounting bracket 76. The surgeon may reference the markings 222 when selecting the mounting bracket 76. To distalize the broach 20 beyond the limits of the mounting brackets 76, the surgeon may attach one of the spacer plates 198 having an appropriate thickness 206 to the depth stop 16 (see FIG. 14). Thus, by attaching the depth stop 16 to the selected mounting bracket 76 and optionally attaching an appropriate spacer plate 198, the surgeon has set the distance 218 between the distal end 36 of the broach 20 and the proximal surface 144 of the depth stop 16. As described above, in a different embodiment, to set the distance 218 the surgeon may choose a depth stop 16 from a number of depth stops 16 having different thicknesses 158, and attach the selected depth stop 16 to the mounting bracket 76.

After attaching the depth stop 16, the surgeon may assemble the intramedullary surgical instrument 12 by threading the distal end 26 of the stem trial 18 onto the tip 30 of the broach 20. The surgeon may also secure the intramedullary surgical instrument 12 to the instrument handle 14 by positioning the central aperture 42 of the broach 20 over the guide pin 78 of the instrument handle 14, engaging the distal surface 40 of the broach 20 with the instrument handle 14, and squeezing the release lever 80 into the clamped position.

The surgeon may align the surgical assembly 10 with the medullary canal 302 of the patient's femur 304 as shown in FIG. 11. To do so, the surgeon aligns the broach axis 46 with an anatomical axis 308 of the femur 304 that extends through a distal opening 310 of the medullary canal 302. The surgeon may then drive the intramedullary surgical instrument 12 into the femur 304 along the anatomical axis 308 by striking the impaction plate 60 of the instrument handle 14 with mallet, sledge, or other impaction tool. As the intramedullary surgical instrument 12 is driven into the bone, the cutting teeth 38 of the broach 20 engage the patient's femur 304 to shape the medullary canal 302 to receive the prosthetic femoral component or a femoral trial component.

Figure 12:
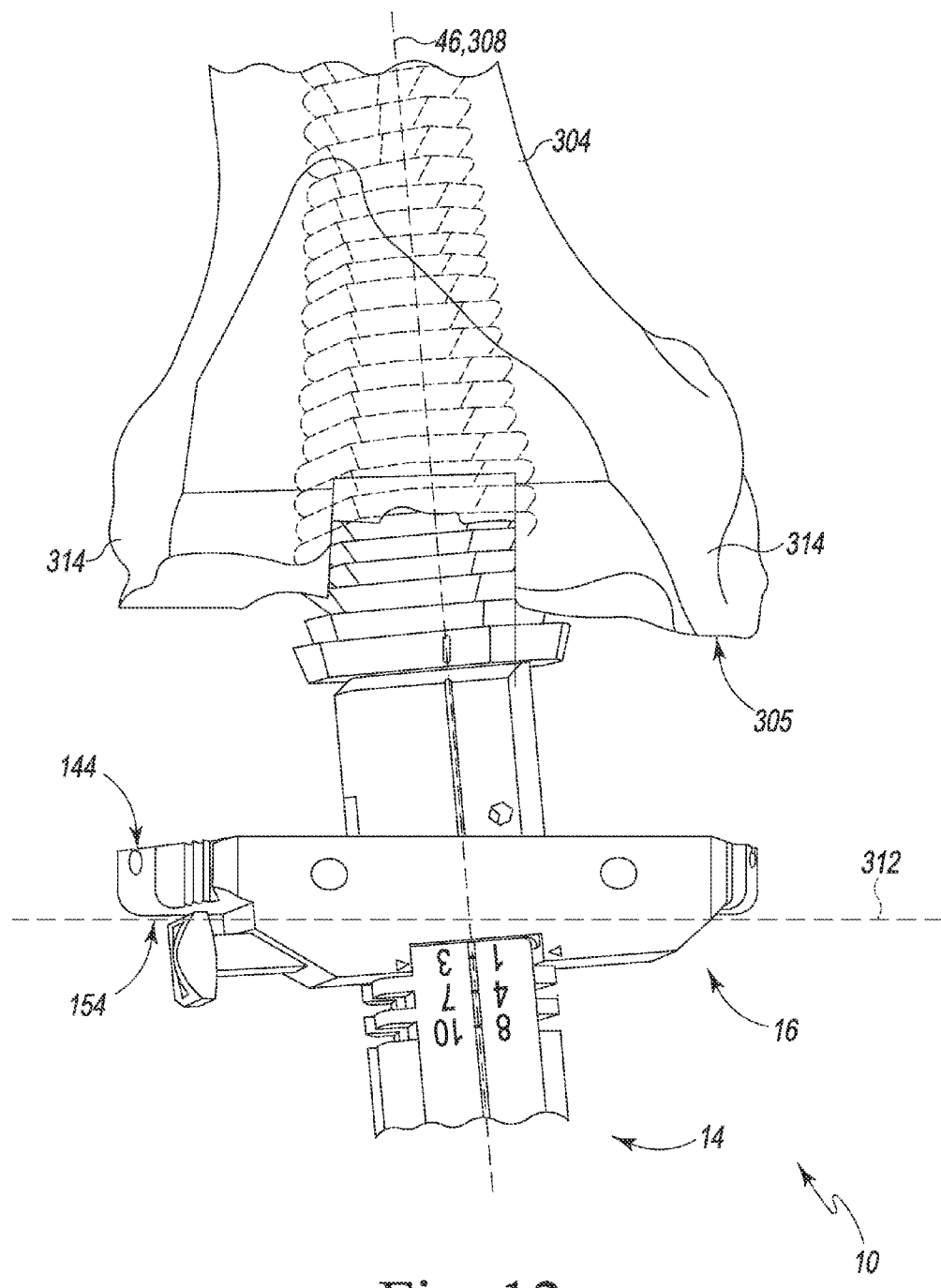

As the intramedullary surgical instrument 12 is advanced into the bone, as shown in FIG. 12, the surgeon may evaluate the position of the intramedullary surgical instrument 12 with respect to the distal surface 306 of the femur 304. The distal surface 154 of the depth stop 16 defines an imaginary joint line 312. The joint line 312 represents the planned contact line between the prosthetic femoral component and the prosthetic tibial bearing of the knee prosthesis. Thus, the surgeon may refer to the joint line 312 when assessing whether the intramedullary surgical instrument 12 is positioned properly in the medullary canal 302. The surgeon may use the distal surface 154 of the base plate 142 as a visual reference for the joint line 312. Additionally, the surgeon may use the curved shape of each of the arms 150 as a visual reference that echoes the shape of the condyles of the prosthetic femoral component. At this stage of the procedure, the surgeon may determine to distalize the broach 20 and attach one of the spacer plates 198 to the depth stop 16 as described above.

Figure 13:
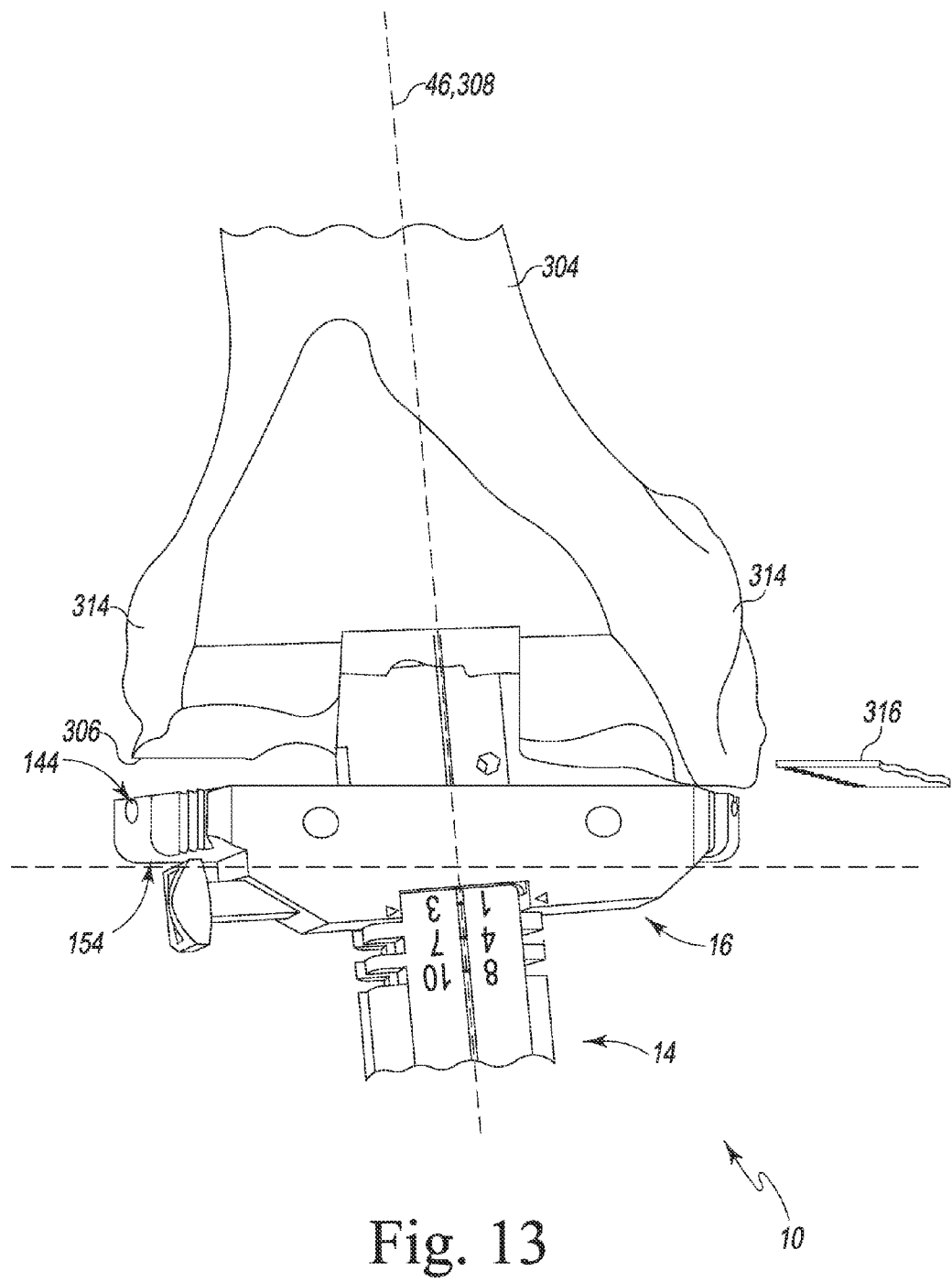

The surgeon may advance the intramedullary surgical instrument 12 into the medullary canal 302 along the anatomical axis 308 of the femur 304 until the proximal surface 144 of the depth stop 16 (or the proximal surface 200 of a spacer plate 198) engages the distal surface 306 of the femur 304 as shown in FIG. 13. If both condyles 314 of the femur 304 are equally distal and free of defects, the proximal surface 144 may contact both condyles 314. If one of the condyles 314 extends further distally than the other condyle 314, the proximal surface 144 may contact the most distal condyle 314, as shown in FIG. 13. When the proximal surface 144 is engaged with the distal surface 306, the distance 218 between the proximal surface 144 and the broach 20 determines the depth of the broach 20 in the medullary canal 302.

Figure 14:
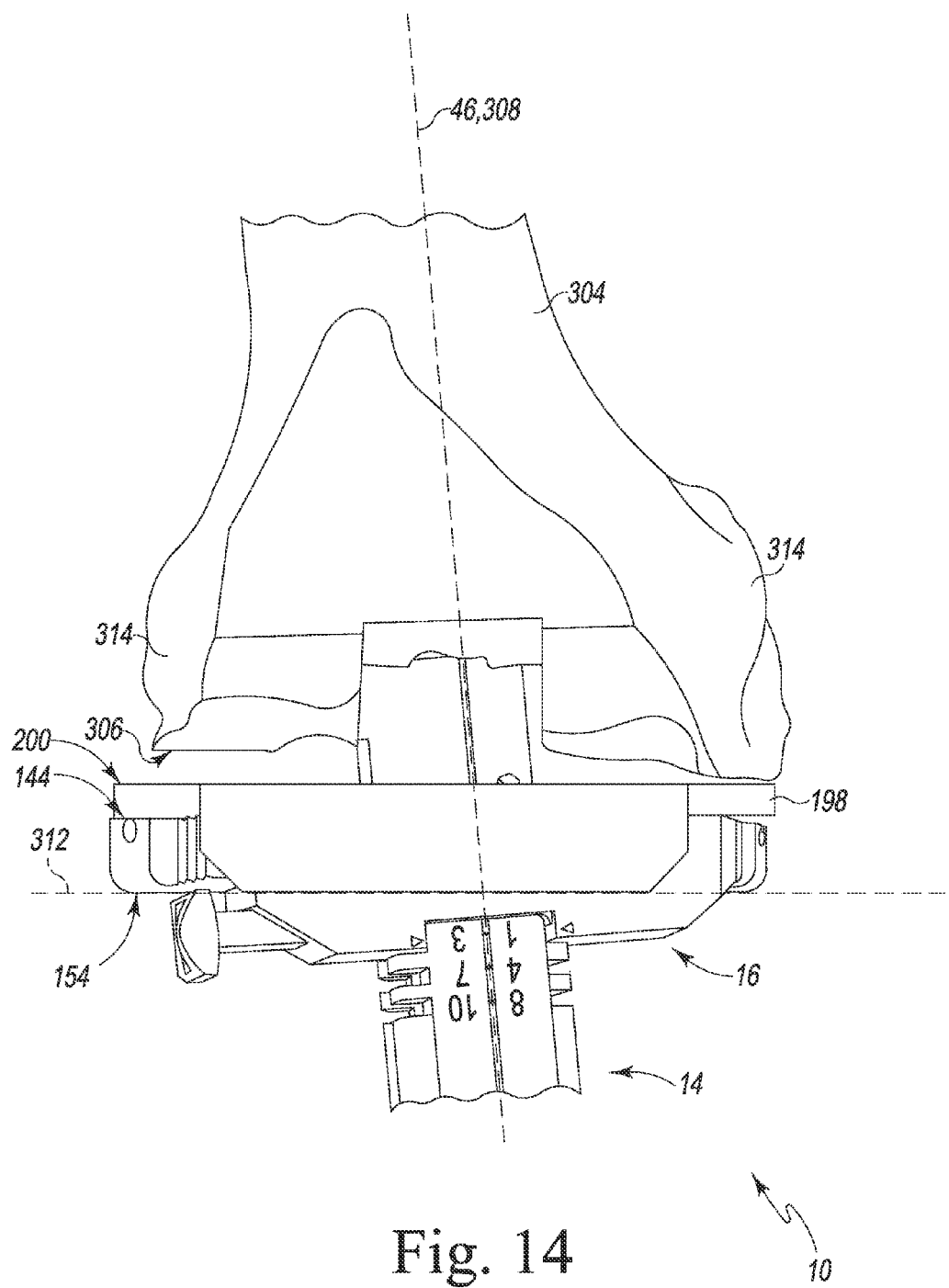

After or during broaching, the surgeon may determine whether to resect the distal surface 306 of the femur 304. The surgeon may determine to resect the distal surface 306 to remove irregularities and provide a clean bone surface for fixation of the prosthetic femoral component. To perform the resection, as shown in FIG. 13, the surgeon may insert a saw blade 316 of a surgical saw between the proximal surface 144 and the distal surface 306 of the femur 304. The surgeon may engage the femur 304 to remove the desired amount of bone, using the proximal surface 144 as a reference. Thus, the proximal surface 144 may act as a non-captured distal cutting guide. As shown in FIG. 14, in some embodiments, a spacer plate 198 may be attached to the depth stop 16. In such embodiments, the proximal surface 200 of the attached spacer plate 198 may used as a non-captured distal cutting guide, similarly to the proximal surface 144. As described above, in some embodiments a captured cutting block may be attached to the broach stop 16 or the spacer plate 198 to perform the resection. After resecting the femur 304, the surgeon may continue to advance the intramedullary surgical instrument 12 along the anatomical axis 308 until the proximal surface 144 (or the proximal surface 200 in some embodiments) engages the freshly cut distal surface 306 of the femur 304, as described above.

Figure 15:
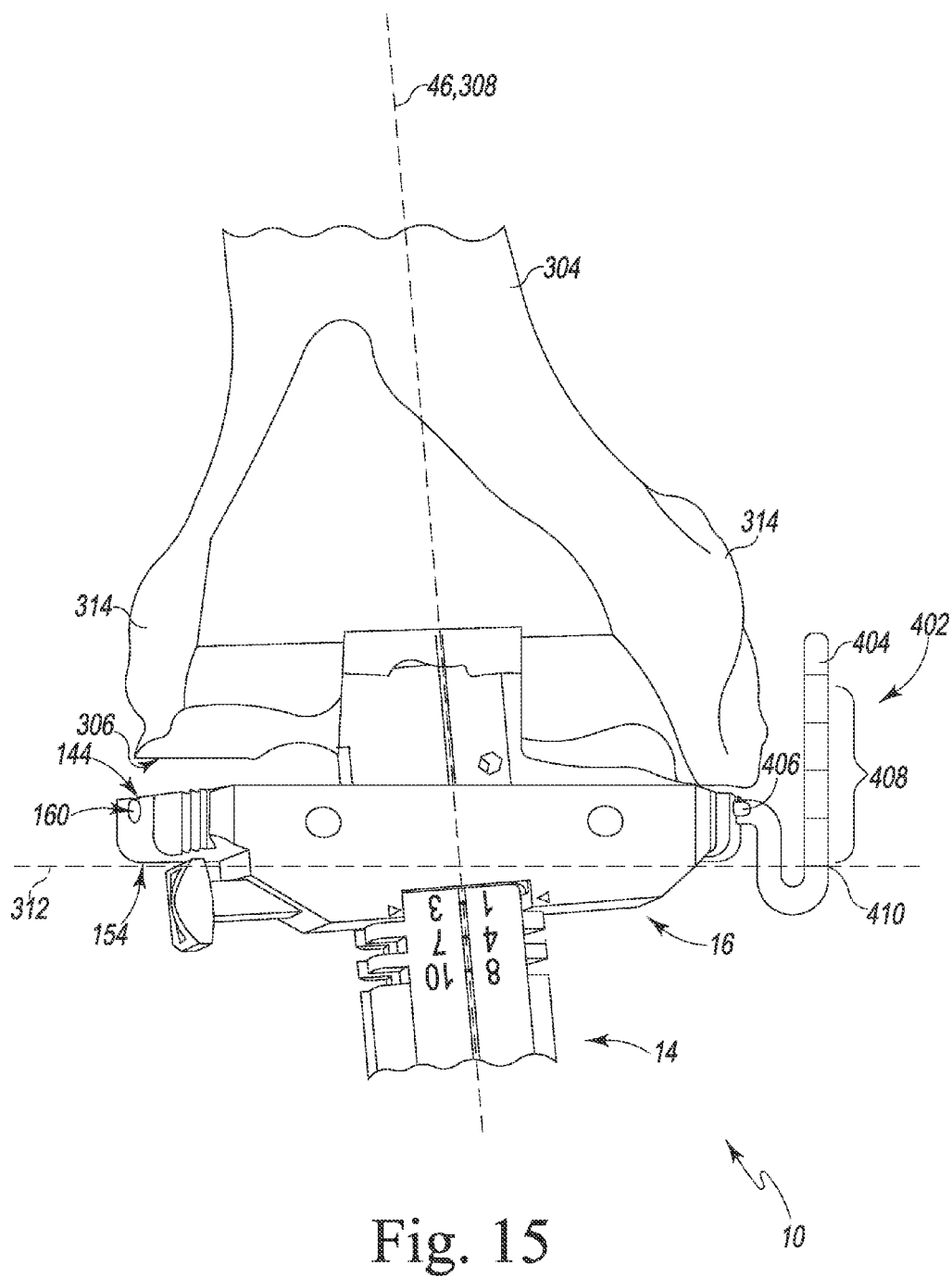

Referring now to FIG. 15, in some embodiments, the surgeon may attach a measurement gauge 402 to the depth stop 16. A measurement gauge suitable for use with the depth stop 16 is shown and described in U.S. patent application Ser. No. 13/780,836 entitled "FEMORAL ORTHOPEDIC SURGICAL INSTRUMENT INCLUDING A MEASUREMENT DEVICE AND METHOD OF USE OF SAME," which is incorporated herein by reference. The measurement gauge 402 includes an arm 404 and a mounting shaft 406 extending from the arm 404. As described above, the mounting shaft 406 of the measurement gauge 402 may slide into the passageway 160 defined in one of the arms 150 of the depth stop 16, thereby securing the measurement gauge 402 to the depth stop 16. The arm 404 of the measurement gauge 402 includes a number of reference markings 408. When secured to the depth stop 16, each of the reference markings indicates a predetermined distance from the joint line 312. The markings 408 include a zero indicator 410 that is aligned with the joint line 312. While advancing the broach 20 into the medullary canal 302, the surgeon may reference the markings 408 to determine the position of the joint line 312 in relation to features of the femur 304, for example, the distal surface 306 or the condyles 314.

After the intramedullary surgical instrument 12 is in position and any resection is complete, the surgeon may further prepare the medullary canal 302 and the femur 304 to receive the prosthetic implant. The surgeon may release the instrument handle 14 from the broach 20 by pulling on the release lever 80, moving the release lever 80 to the unlocked position. After removing the instrument handle 14, the intramedullary surgical instrument 12 remains seated within the medullary canal 302. As shown in FIG. 16, the surgeon may secure an intramedullary adapter 412 to the intramedullary surgical instrument 12. The intramedullary adapter 412 is a surgical tool configured to be secured to the intramedullary surgical instrument 12 and including an end sized and shaped to be positioned in a medullary canal of a patient's femur during the orthopedic surgical procedure. To secure the intramedullary adapter 412 to the intramedullary surgical instrument 12, the surgeon may engage a captured bolt 414 of the intramedullary adapter 412 with the central aperture 42 of the broach 20 and tighten the captured bolt 414. The central aperture 42 may include a threaded inner surface configured to receive the captured bolt 414.

The surgeon may further attach a modular cutting block 416 to the intramedullary adapter 412. The modular cutting block 416 includes a base plate 418 and a pair of curved arms 420 that extend posteriorly from the base plate 418. Each of the curved arms 420 may correspond to a condylar surface of the prosthetic femoral component. The modular cutting block 416 further includes a number of cutting guides 422 that the surgeon may use to prepare the distal surface 306 of the patient's femur 304. The surgeon may attach additional sub-modules to the modular cutting block 416 to perform additional cuts to prepare the patient's femur 304 (not illustrated).

After installing the modular cutting block 416, the surgeon may use a gap assessment tool 424 to assess the position of the femur 304 in relation to the patient's tibia 318. The gap assessment tool 424 may be used to assess the joint space between a patient's femur 304 and tibia 318 including, for example, the flexion and extension gaps of the patient, and the size the prosthetic implants. After completing preparation of the femur 304, the surgeon may loosen the captured bolt 414 and remove the intramedullary adapter 412 and the modular cutting block 416 from the patient's femur 304.

Last, after completing preparation of the patient's femur 304, the surgeon may reattach the instrument handle 14 to the broach 20 and remove the intramedullary surgical instrument 12 from the medullary canal 302. After removal, the surgeon may proceed with implantation of prosthetic components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method for surgically preparing a distal end of a femur to receive an orthopedic prosthesis, the method comprising:
   attaching a depth stop to a handle at a first position of a plurality of positions along an elongated body of the handle,
   securing a broach to an end of the handle, the broach having a tapered outer surface with a plurality of cutting teeth defined in the outer surface,
   advancing the broach along an anatomical axis of the femur through a distal opening of a medullary canal of the femur, and
   engaging a proximal surface of the depth stop with a distal surface of the femur, wherein an oblique angle is defined between the proximal surface and the anatomical axis of the femur.

2. The method of claim 1, wherein engaging the proximal surface includes engaging the proximal surface such that the oblique angle has a magnitude of approximately eighty-five degrees.

3. The method of claim 1, further including:
   planning a depth of the broach in relation to the distal surface of the femur, and
   selecting the first position of the plurality of positions based on the planned depth of the broach,
   wherein engaging the proximal surface includes engaging the proximal surface when the broach is positioned in the medullary canal at the planned depth.

4. The method of claim 3, wherein planning the depth of the broach includes planning the depth based on a size of the orthopedic prosthesis to be implanted.

5. The method of claim 1, further including:
   engaging a non-captured cutting guide of the proximal surface of the depth stop to resect the distal end of the femur,
   advancing the broach along an anatomical axis of the femur after resecting the distal end, and
   engaging the proximal surface of the depth stop with the distal surface of the femur after resecting the distal end.

6. The method of claim 5, further including:
   planning a depth of the broach in relation to the distal surface of the femur,
   selecting a spacer plate from a plurality of spacer plates based on the planned depth, the spacer plate having a proximal surface that defines a non-captured distal cutting guide, and
   attaching the spacer plate to the depth stop such that the proximal surface of the spacer plate is the proximal surface of the depth stop.

* * * * *